US012797397B2

(12) United States Patent
Zhang et al.

(10) Patent No.: US 12,797,397 B2
(45) Date of Patent: Nov. 17, 2026

(54) DRUG TARGET FOR INHIBITING TUMOR, USE, AND ORAL DRUG

(71) Applicant: CHI BIOTECH CO., LTD., Guangdong (CN)

(72) Inventors: Gong Zhang, Guangdong (CN); Yang Chen, Guangdong (CN); Zhuo Yu, Guangdong (CN)

(73) Assignee: CHI BIOTECH CO., LTD., Guangdong (CN)

( * ) Notice: Subject to any disclaimer, the term of this patent is extended or adjusted under 35 U.S.C. 154(b) by 362 days.

(21) Appl. No.: 18/406,047

(22) Filed: Jan. 5, 2024

(65) Prior Publication Data

US 2025/0222011 A1 Jul. 10, 2025

(51) Int. Cl.

*A61K 9/00* (2006.01)
*A61K 31/603* (2006.01)

(52) U.S. Cl.

CPC .......... *A61K 31/603* (2013.01); *A61K 9/0053* (2013.01)

(58) Field of Classification Search

CPC ............................ A61K 9/0053; A61K 31/603
See application file for complete search history.

(56) References Cited

FOREIGN PATENT DOCUMENTS

| | | | | |
|---|---|---|---|---|
| AU | 20222472191 | * | 6/2024 | ........... A61K 31/192 |
| CN | 107912043 A | | 4/2018 | |
| CN | 110638802 A | | 1/2020 | |

OTHER PUBLICATIONS

"The initiation Factor elF2 Related to Tumorigenesis ", Fan Daiming-editor, vol. 5, Frontiers in Oncology, Xi'an: Xi'an Jiaotong University Press, first edition, p. 67, with English Translation.
Dmitriev S. E. et al., "A Quick Guide to Small-Molecule Ihibitors of Eukaryotic Protein Synthesis", Biochemistry (Moscow) , vol. 85, No. 11, p. 1389 to p. 1421.
Chinese First Office Action for application No. 202211457404.4 dated Oct. 23, 2023 with English Translation.
Trott, et al., "AutoDock Vina: improving the speed and accuracy of docking with a new scoring function, efficient optimization and multithreading", J Comput Chem. Jan. 30, 2010; 31(2): 455-461. doi:10.1002/jcc21334.
Wang et al., "Translating mRNAs strongly correlate to proteins in a multivariate manner and their translation ratios are phenotype specific", Nucleic Acids Research, 2013, vol. 41, No. 9 4743-4754.
Zebrucka, et al., "The integrated stress response", EMBO reports vol. 17 | No. 10 | 2016, pp. 1374-1395.
Li, et al., "Optimal Settings of Mass Spectrometry Open Search Strategy for Higher Confidence", J. Proteome Res. 2018, 17, pp. 3719-3729.
Adomavicius, et al., "The structural basis of translational control by elF2 Phosphorylation", Nature Communications | (2019) 10:2136.
Naineni, et al., "A comparative study of small molecules targeting elF4A", RNA (2020) 26: Published by Cold Spring Harbor Laboratory Press for the RNA Society, pp. 541-549.
Chen, et al. "EIF2A promotes cell survival during paclitaxel treatment in vitro and in vivo", J Cell Mol Med. 2019;23:6060-6071.

* cited by examiner

*Primary Examiner* — Erich A Leeser
(74) *Attorney, Agent, or Firm* — Carter, DeLuca & Farrell, LLP

(57) ABSTRACT

The present disclosure relates to the technical field of targeted drug development, and in particular to a drug target for inhibiting a tumor and use thereof. Specifically, the present disclosure provides a drug target for inhibiting a tumor, where the drug target is a eukaryotic initiation factor 2 (EIF2). The present disclosure further provides use of the drug target for inhibiting a tumor and an oral drug. In the present disclosure, the drug target inhibits the initiation of translation in a eukaryotic cell by inhibiting translation of the EIF2, thereby safely suppressing a malignant phenotype of cancer cells.

8 Claims, 5 Drawing Sheets

DRUG TARGET FOR INHIBITING TUMOR, USE, AND ORAL DRUG

TECHNICAL FIELD

The present disclosure relates to the technical field of targeted drug development, and in particular to a drug target for inhibiting a tumor, use, and an oral drug.

BACKGROUND

Inhibition of cancer cell translation can effectively suppress cancer cell growth and shows a drug development value. However, inhibition of the translation may result in severe cytotoxicity. Translation inhibitors occupy ribosome resources, and cause cellular stress and protein folding disorders, affecting the clinical application prospects of translation inhibition-related drugs.

Currently, inhibitory small-molecule compounds or mimetics have been developed in related technologies to affect the enzymatic activity, functional structure, and modification abundance of individual eukaryotic initiation factors (EIFs), thereby inhibiting the translation initiation. For example, Elatol, SAN, and 15d-PGJ2 have been developed to inhibit EIF4A1 (PMID: 32014999). However, such inhibitors can easily cause integrated stress response on cells (ISR) (PMID: 32014999). The ISR, as an adaptive cellular mechanism, can non-specifically inhibit overall cell protein synthesis, thus allowing cells to respond to stress and survive (PMID: 27629041).

A key to the ISR is phosphorylation of eIF2a, which serves to inhibit the overall cell protein synthesis while allowing expression of selected mRNAs. Although the ISR is primarily a homeostatic program that promotes survival, the exposure to severe stress drives signaling to cell death, resulting in cytotoxicity. For example, it has been reported that paclitaxel treatment in breast cancer treatment can induce the ISR to provide a survival advantage for cancer in vivo (PMID: 31211507). ISR can translate internal ribosome entry site (IRES)-dependent upstream open reading frame (uORF) proteins. For example, cancer-promoting genes including SOX2, MYC, and HER2 can be preferentially translated under ISR induction, allowing cancer cells to resist adversity and then leading to drug resistance and recurrence of cancer.

As a result, there is still an urgent need in this field to find a suitable drug target to achieve precise targeted therapy of the cancer.

SUMMARY

In view of this, the present disclosure aims to provide a drug target capable of effectively inhibiting a tumor, especially malignant phenotypes including proliferation, metastasis, and tumor formation of cancer cells, thereby achieving precise targeted therapy of the cancer while avoiding side effects.

In a first aspect, the present disclosure provides a drug target for inhibiting a tumor, where the drug target is a eukaryotic initiation factor 2 (EIF2). The EIF2 is a protein complex composed of multiple constituent proteins and has a structure shown in the literature from Tomas Adomavicius et al. ("The structural basis of translational control by eIF2 phosphorylation", *Nature Communication*, May 13, 2019, Article number: 2136 (2019), https://www.nature.com/articles/s41467-019-10167-3). In some examples, the drug target is an EIF2 subunit 1 (EIF2S1). For example, the EIF2S1 has a protein sequence referring to Ref Seq ID: NP_004085 of the National Center of Biotechnology Information (NCBI) library. In some examples, the drug is selected from the group consisting of aurintricarboxylic acid (ATCA) and an ammonium salt thereof.

The ISR can be inhibited by inhibiting the EIF2 to effectively reduce its phosphorylation. Meanwhile, inhibiting the EIF2 can prevent the assembly of ribosomes for translation initiation, so that it does not consume ribosome resources, and is therefore less likely to produce various stress reactions in cells, thereby safely inhibiting cancer cells.

In some examples, the tumor is a malignant tumor selected from the group consisting of a malignant epithelial tumor, sarcoma, myeloma, leukemia, lymphoma, melanoma, a head and neck tumor, a brain tumor, peritoneal cancer, a mixed tumor, and a malignant childhood tumor.

In some examples, the malignant epithelial tumor is selected from the group consisting of lung cancer, breast cancer, liver cancer, pancreatic cancer, colorectal cancer, gastric cancer, gastroesophageal adenocarcinoma, esophageal cancer, small intestine cancer, esophageal and cardiac cancer, endometrial cancer, ovarian cancer, fallopian tube cancer, vulvar cancer, testicular cancer, prostate cancer, penile cancer, kidney cancer, bladder cancer, anal cancer, gallbladder cancer, bile duct cancer, teratoma, and cardiac tumor.

In some examples, the tumor is lung cancer, preferably non-small cell lung cancer.

In some examples, the tumor is ovarian cancer, preferably ovarian epithelial cancer.

In some examples, the tumor is liver cancer.

In a second aspect, the present disclosure provides use of an EIF2 as a drug target for inhibiting a tumor.

In some examples, the drug is selected from the group consisting of aurintricarboxylic acid (ATCA) and an ammonium salt thereof.

In a third aspect, the present disclosure provides use of a substance for inhibiting EIF2 in preparation of a drug for treating a tumor.

In some examples, the substance is selected from the group consisting of ATCA and an ammonium salt thereof.

In a fourth aspect, the present disclosure provides an oral drug for inhibiting a tumor, including an inhibitor capable of targeting and then inhibiting a drug target EIF2 without causing phosphorylation. In some examples, the inhibitor is selected from the group consisting of ATCA and an ammonium salt thereof.

To sum up, the present disclosure can achieve the following beneficial technical effects.

In the present disclosure, the drug target inhibits the initiation of translation in a eukaryotic cell by inhibiting translation of the EIF2, thereby safely suppressing a malignant phenotype of cancer cells. The present disclosure at least achieves the following safety features:

1. Unlike other commonly-used translation initiation inhibitors (including cycloheximide (CHX) and harringtonine), the drug target does not occupy ribosome resources when targeting the EIF2 and can competitively bind to ribosomes. For example, the CHX not only inhibits translation initiation, but also inhibits translation elongation, thus stimulating more stress responses and causing greater side effects.
2. The drug target does not cause integrated stress response (ISR) in cells and can reduce toxic and side effects on normal cells.

3. The oral drug based on the drug target is safe to be taken orally.

DETAILED DESCRIPTION OF THE EMBODIMENTS

Figure 1:
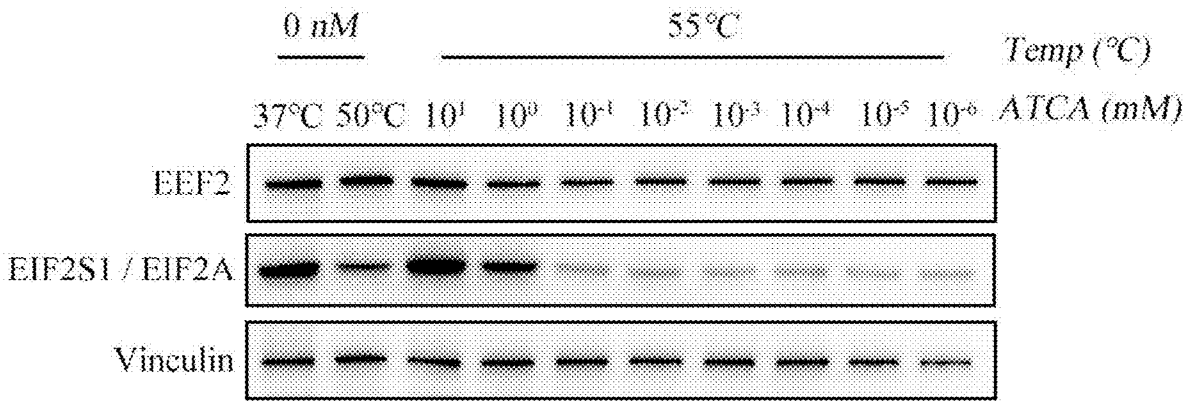
FIG. 1 shows a cellular thermal shift assay-Western blotting (CESTA-WB) image of ATCA binding to EIF2S1.

The present disclosure is described in further detail below with reference to the accompanying drawings and specific examples.

In order to develop drugs that can effectively inhibit translation of cancer cells, a large amount of research has been conducted in the present disclosure. The results have unexpectedly found that inhibition of the EIF2 can effectively reduce phosphorylation thereof, thereby inhibiting ISR. Moreover, inhibiting the EIF2 can prevent the assembly of ribosomes for translation initiation, does not consume ribosome resources, and is less likely to produce various stress reactions in cells, thereby safely inhibiting cancer cells.

In addition, during the research of the present disclosure, it is found that ATCA can target and bind to the EIF2 subunit EIF2S1, but does not affect its phosphorylation abundance, which means that the ATCA does not cause ISR. The downregulation of SOX2 and HER2 expression indicates that the cells do not undergo the small uORF events of ISR-dependent SOX2 and HER2 triggered by EIF2S1. Further, experiments have shown that the ATCA only targets and binds to the EIF2 subunit EIF2S1, but does not bind to non-target proteins EEF2 and Vinculin.

Based on the above findings, the present disclosure is completed.

The technical solutions of the present disclosure will be described in detail below with reference of to specific examples. Those of ordinary skill in the prior art will appreciate that these examples are provided merely to illustrate some exemplary ways in which the present disclosure may be practiced, and are not intended to limit the scope of the present disclosure to these exemplary embodiments.

Example 1: CESTA-WB Experiment

CESTA-WB experiment: H1299 cells were plated and cultured in a 15 cm dish, and when a cell density reached about 90% to 100%, the medium was aspirated; the cells were washed twice with PBS, and 2 mL of Lysis Buffer (RB Buffer, 10% N-Dodecyl-β-D-maltoside, and 1× protease inhibitor) was added to each dish and placed flatly on ice to allow lysis for 30 min, and a cell lysate was collected and centrifuged at 17,000 g, 4° C. for 10 min; a resulting supernatant was quantified using a BCA kit. 45 μL of a whole protein was added in a PCR tube, ATCA was added to final concentrations of 10 mM, 1 mM, 100 μM, 10 μM, 1 μM, 100 nM, and 10 nM, respectively, and allowed to stand at 25° C. for 30 min to allow the ATCA to fully interact with the whole protein; while another two tubes without ATCA were taken as controls. The experimental group was treated at 55° C. for 3 min, while one tube in the control group was treated at 37° C. for 3 min, and the other tube was treated at 50° C. for 3 min; centrifugation was conducted at 17,000×g for 10 min at 4° C. to remove denatured proteins. The supernatant was transferred into a new PCR tube, and 5 μg of the supernatant was added into 5×SDS Loading Buffer to allow denaturation in a 100° C. water bath; the Western Blotting was conducted to quantify EEF2, EIF2S1, B-actin, and Vinculin proteins.

Western Blotting experiment: the sample and molecular weight standard of pre-stained protein were loaded onto an SDS-PAGE gel (10 cmx 10 cm) to allow electrophoresis at 100 V for 40 min. The proteins in SDS-PAGE were transferred to nitrocellulose membrane at 100 V, 230 mA within 1 h. After transfer, the nitrocellulose membrane was washed with 25 mL of TBS for 5 min at room temperature. The nitrocellulose membrane was placed in 25 mL of blocking buffer (TBST, 5% skim milk) and incubated at room temperature for 1 h. The membrane was washed three times with 15 mL TBST, 5 min each. The membrane and EEF2, EIF2S1, B-actin, and Vinculin primary antibodies (diluted at 1:1500) were placed in 10 mL of a primary antibody dilution buffer and incubated overnight at 4° C. with gentle shaking. The membrane was washed three times with 15 mL TBST, 5 min each. A rabbit secondary antibody was prepared with 5% skim milk at a ratio of 1:2000 and incubated at room temperature for 1.5 h. The membrane was washed three times with 15 mL TBST, 5 min each time. The membrane was incubated with 10 mL of LumiGLO® (0.5 mL 20× LumiGLO® #7003, 0.5 mL 20× peroxide, and 9.0 mL purified water) at room temperature for 1 min with gentle agitation at intervals. The excess developer on the membrane was drained (no drying), wrapped in plastic film, and then developed with a BIO-RAD imager. The results were shown in FIG. 1.

As shown in FIG. 1, ATCA binds to its target protein EIF2S1 (one of the constituent proteins of eIF2), but did not bind to the non-target proteins EEF2 and Vinculin.

Example 2 Molecular Docking Analysis: Evaluating the Binding Energy and Interaction Mode of ATCA and Target Protein EIF2S1 Thereof In order to evaluate the binding energy and interaction mode of ATCA and target protein EIF2S1 thereof, protein-ligand docking analysis was performed with AutoDockVina 1.2.2 (PMID: 19499576). A molecular structure of ATCA was obtained from the PubChem compound database (https://pubchem.ncbi.nlm.nih.gov/), as shown in the following formula (1).

Formula (1)

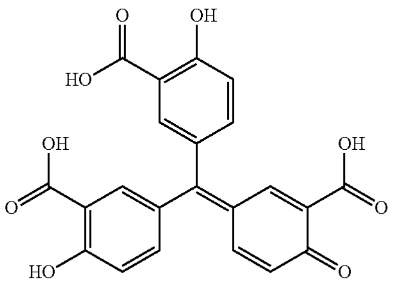

The 3D coordinates of protein EIF2S1 (PDB number: 6ybv; resolution: 3.8 Å) were downloaded from PDB (https://www.rcsb.org/). The protein and ligand files were prepared, all protein and molecule files were converted into PDBQI format, all water molecules were removed, and polar amino acid atoms were added. The grid boxes were centered to cover the structural domains of each protein and accommodated free molecular motion. The docking pocket was set as a square pocket of 30 Å×30 Å×30 Å, and the grid distance is: 0.05 nm. The molecular docking analysis was used for model visualization with AutoDock Vina 1.2.2 (http://autodock.scripps.edu/). The analysis results were shown in FIG. 2.

Figure 2:
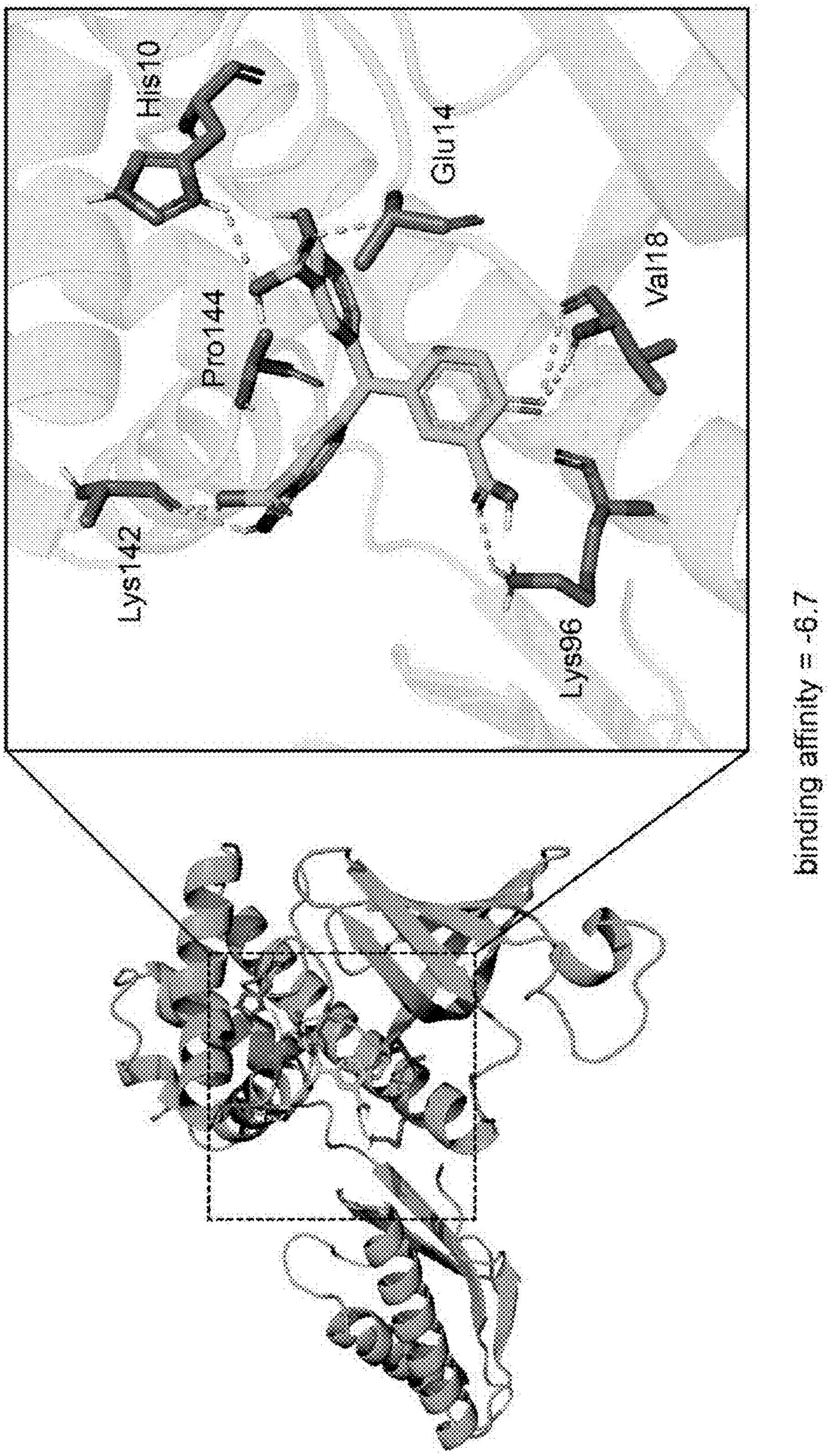
FIG. 2 shows a schematic diagram of molecular docking to evaluate binding energy and interaction mode of the ATCA and target protein EIF2S1 thereof.

As shown in FIG. 2, the molecular docking results showed the most stable docking conformation. The ATCA could penetrate deep into the interior of the EIF2S1 pocket to form multiple stable hydrogen bonds with Lys142, Pro144, His10, Lys96, and Val18 subunits, with a binding energy of −6.7 kcal/mol. This indicated that ATCA could form an effective non-covalent binding and occupy pocket site of EIF, inhibiting EIF function, and could be dissociated, forming a competitive binding. In this way, the degree of inhibition of EIF2S1 was easily adjusted by adjusting the concentration of ATCA, or the inhibition of EIF2S1 was released by removing ATCA, achieving flexible control on demand.

Example 3: Western Blotting Detection of EIF2A Phosphorylation

Western Blotting method: the sample and molecular weight standard of pre-stained protein were loaded onto an SDS-PAGE gel (10 cm×10 cm) to allow electrophoresis at 100 V for 40 min. After treating for 1 h at 100 V, 230 mA, the protein in SDS-PAGE was transferred to a nitrocellulose membrane. After transfer, the nitrocellulose membrane was washed with 25 mL of TBS for 5 min at room temperature. The nitrocellulose membrane was placed in 25 mL of blocking buffer (TBST, 5% skim milk) and incubated at room temperature for 1 h. The membrane was washed three times with 15 mL TBST, 5 min each time. The membrane and phosphorylated EIF2S1 primary antibody (diluted at 1:1500) were placed in 10 mL of a primary antibody dilution buffer and incubated overnight at 4° C. with gentle shaking at certain intervals. The membrane was washed three times with 15 mL TBST, 5 min each time. A rabbit secondary antibody was prepared with 5% skim milk at a ratio of 1:2000 and incubated at room temperature for 1.5 h. The membrane was washed three times with 15 mL TBST, 5 min each time. The membrane was incubated with 10 mL of LumiGLO® (0.5 mL 20× LumiGLO®, 0.5 mL 20× peroxide, and 9.0 mL purified water) at room temperature for 1 min with gentle agitation at certain intervals. The excess developer on the membrane was drained (no drying), wrapped in plastic film, and then developed with a BIO-RAD developer.

Figure 3:
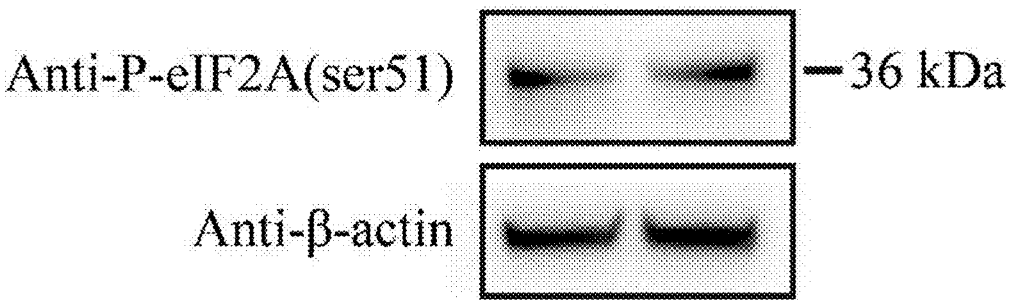
FIG. 3 shows results of Western blotting detection of EIF2A phosphorylation, where a left lane is a control, and a right lane is a result after treatment with 1 mM of ATCA for 48 h.
Figure 4:
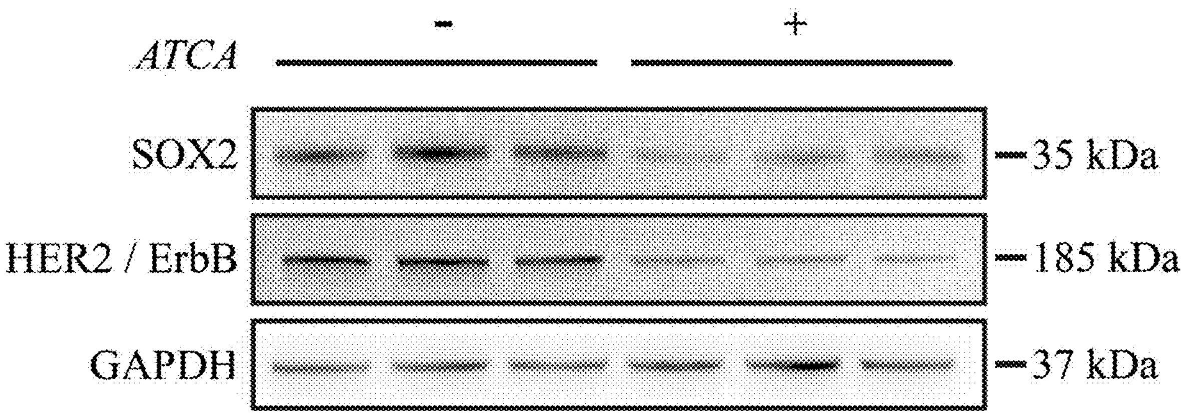
FIG. 4 shows a electropherogram illustrating down-regulation of SOX2 and HER2 after ATCA treatment.

The results were shown in FIG. 3 and FIG. 4. As shown in FIG. 3, the ATCA could target and bind to EIF2S1 but did not affect its phosphorylation abundance, indicating no ISR caused. As shown in FIG. 4, the downregulation of SOX2 and HER2 expression indicated that the cells did not undergo the small uORF events of ISR-dependent SOX2 and HER2 triggered by EIF2S1.

Figure 5:
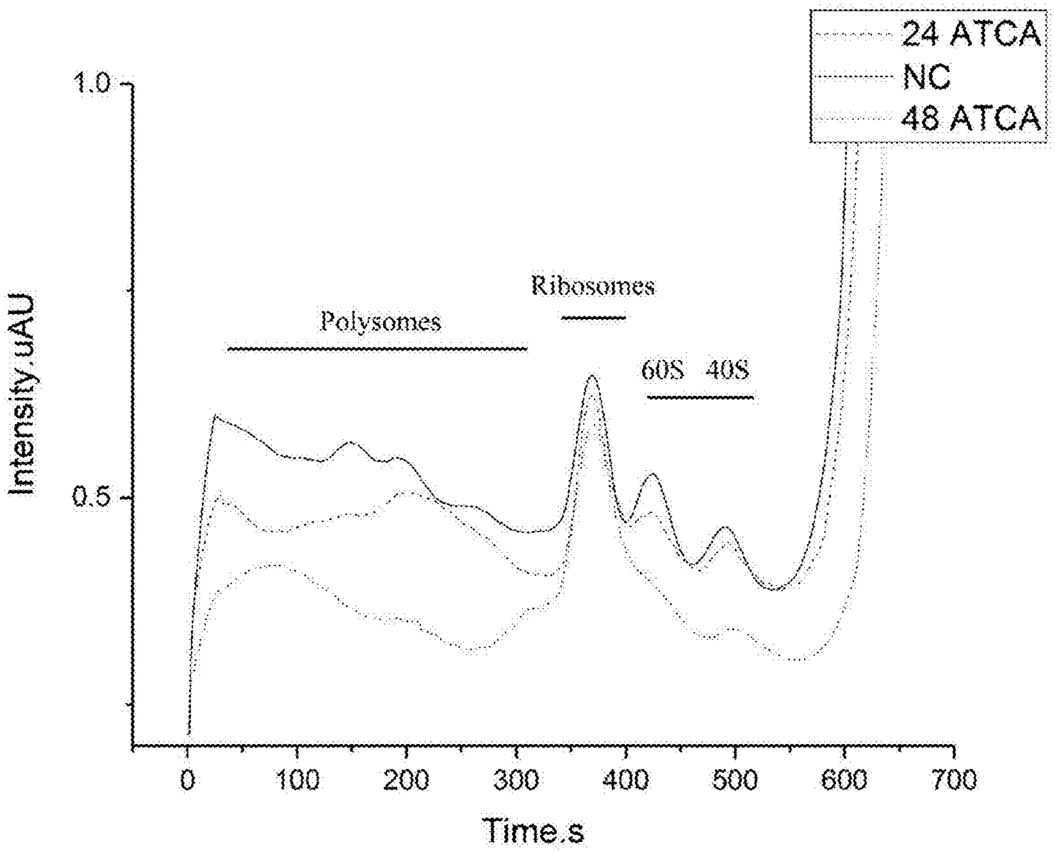
FIG. 5 shows results of a polysome analysis experiment.

Example 4: Cell Translation Initiation Efficiency Determination and Nascent Peptide Detection Polysome profiling: cells were plated in a 75 T flask with 2 million cells per flask and allowed to adhere for 24 h, and the ACTA was added to the experimental group to make a concentration of the working solution at 1 mg/mL. The control group was replaced with a new medium. Samples were collected after 24 h and 48 h of ATCA treatment. The medium was aspirated, the samples were washed twice with PBS, and 2 mL of Lysis Buffer (RB Buffer, 1% Ttiton X-100, and 10 μg/μL cycloheximide) was added to allow lysis for 30 min on ice, and a resulting lysate was pipetted into an RNase-free EP tube. After centrifugation for 10 min at 4° C. and 17,000 g, 1.5 mL of a resulting supernatant was pipetted into a new EP tube and added into a pre-prepared sucrose density gradient solution (sucrose concentrations from top to bottom: 13% to 46%, and each gradient was successively increased by a concentration of 3%). After centrifugation for 4 h and 10 min at 4° C. and 25,400 rpm, high-performance liquid chromatography (HPLC) was conducted to allow relative quantitative analysis of polyribosomes, monoribosomes, and large and small subunits of ribosomes. The results were shown in FIG. 5. As shown in FIG. 5, 24 h after adding the drug, the polysome distribution curve did not change much; 48 h after adding the drug, the polyribosome fraction was significantly reduced and mainly existed in the form of monoribosomes. ATCA did not affect translation elongation, indicating that translation initiation had been effectively slowed down, resulting in only one ribosome translating most of mRNAs.

Detection of nascent peptides: the cells were plated in a 6-well plate, with 200,000 cells in each well. After 24 h of adhesion, ATCA was added to make a working solution at a concentration of 1 mg/mL, while the control group was replaced with new medium. The experimental and control groups were treated for 2 h, 6 h, 12 h, 24 h, and 48 h separately, while ATCA was added to the control group, and cycloheximide was added to the positive control group for 10 min of treatment 25 min before sample collection. 10 μg/μL puromycin-labeled nascent peptide was added to all wells for 15 min, the medium was aspirated, the cells were washed twice with PBS, added with IP & WB lysis buffer to allow lysis on ice for 30 min, and centrifuged at 12,000 g for 20 min at 4° C. A resulting supernatant was transferred to a new centrifuge tube, 10 μg of protein was added to 5×SDS Loading Buffer, denatured in a 100° C. water bath for 10 min, and quantitatively detected by Western blotting.

Western Blotting: the sample and molecular standard of pre-stained protein were loaded onto an SDS-PAGE gel (10 cm×10 cm) to allow electrophoresis at 100 V for 40 min. The proteins in SDS-PAGE were transferred to nitrocellulose membrane at 100 V, 230 mA within 1 h. After transfer, the nitrocellulose membrane was washed with 25 mL of TBS for 5 min at room temperature. The nitrocellulose membrane was placed in 25 mL of blocking buffer (TBST, 5% skim milk) and incubated at room temperature for 1 h. The membrane was washed three times with 15 mL TBST, 5 min each time. The membrane and puromycin primary antibody (diluted at 1:1000) were placed in 10 mL of a primary antibody dilution buffer and incubated overnight at 4° C. with gentle shaking at intervals. The membrane was washed three times with 15 mL TBST, 5 min each time. A rabbit secondary antibody was prepared with 5% skim milk at a ratio of 1:2000 and incubated at room temperature for 1.5 h. The membrane was washed three times with 15 mL TBST, 5 min each time. The membrane was incubated with 10 mL of LumiGLO® (0.5 mL 20× LumiGLO®, 0.5 mL 20× peroxide, and 9.0 mL purified water) at room temperature for 1 min intended to When agitation at intervals. The excess developer on the membrane was drained (not drying), wrapped in plastic film, and developed with a BIO-RAD developer. The results were shown in FIG. 6.

Figure 6:
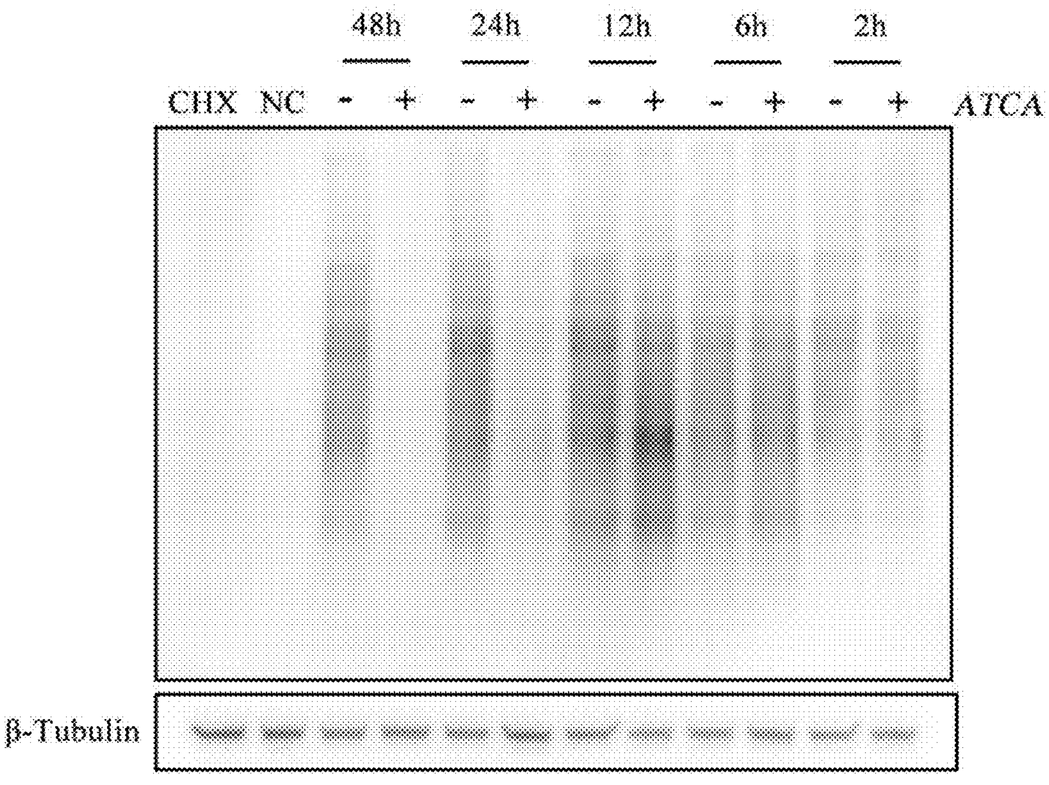
FIG. 6 shows a Western blotting diagram for detecting nascent peptides.

As shown in FIG. 6, puromycin could covalently bind itself as an "amino acid" to the end of the nascent peptide chain and fell off from the ribosome. Puromycin antibodies could be used to see these nascent peptides with puromycin at the end. FIG. 6 showed that protein synthesis had not been significantly blocked after adding the drug for 2 h to 12 h; after adding the drug for 24 h to 48 h, the number of new peptide chains was significantly reduced compared with that without the drug, proving that ATCA's ability to inhibit translation initiation could effectively reduce protein synthesis.

Example 5: Transcriptome Sequencing

Experimental Steps for Transcriptome Sequencing

Extraction of RNA 1 mg/mL ATCA was added to the culture medium of a T75 cell culture flask filled with three million of H1299 cells as a treatment group, and an equal volume of PBS was added as a control group. After ATCA treatment for 48 h, the cultured supernatant was discarded, and the cells were placed on ice, washed twice with pre-cooled PBS. The PBS was discarded, 5 mL of pre-cooled Trizol (total RNA extraction reagent) was added, mixed by shaking thoroughly. The specific extraction operations were as follows:

1) 0.2 mL of chloroform was added into every 1000 μL of Trizol, mixed well vigorously (can be vortexed) for 15 s, and allowed to stand at room temperature for 3 min to observe that the sample began to stratify;
2) the sample was centrifuged at 12,000×g for 15 min at 4° C. to separate into three layers;
3) about 600 μL of an upper aqueous phase was carefully transferred to a new 1.5 mL EP tube, without pipetting a middle-layer liquid;
4) 800 μL of isopropanol was added to the sample, and mixed well by inverting;
5) a resulting mixture was allowed to stand at −20° C. for 8 h;
6) after 8 h, centrifugation was conducted at 12,000×g and 4° C. for 30 min to remove the supernatant;
7) 1 mL of 75% ethanol (pre-cooled at −20° C. for 30 min) was added;
8) centrifugation was conducted at 7,500×g and 4° C. for 5 min to remove the supernatant;
9) repeat steps 7) to 8);
10) the remaining ethanol was removed, and a tube cover was opened to allow air-drying for 5 min; and
11) obtained pellet was dissolved with about 30 μL to 60 μL of RNase-free pure water according to a particle size, and an RNA standard obtained in this step was stored in a −80° refrigerator.

Poly-AmRNA Enrichment:

The experiment was conducted in accordance with the human poly-A mRNA standard transcriptome library construction and sequencing process. The specific experimental steps were referred to the applicant's published literatures (PMID: 23519614, PMID: 30265008).

This process adopted poly-A mRNA enrichment kit from Vazyme Biotech to enrich poly-A mRNA. The specific steps were shown in the instructions: the total poly-A mRNA was extracted using the VAHTS mRNA Capture Beads kit, including:

1) the mRNA Capture Beads were taken out and allowed to stand until their temperature equilibrated to room temperature;
2) preparation of an RNA sample: 0.01 μg to 12.5 μg of total RNA was diluted to 50 μL with RNase-free water in a Nuclease-free PCR tube, and placed on ice for later use;
3) the mRNA Capture Beads were placed upside down to mix thoroughly, and 50 μL of same was added to the total RNA sample and mixed well;
4) the sample was incubated in a PCR machine at 65° C. for 5 min and then 25° C. for 5 min, and maintained at 4° C. to allow the mRNA to bind to the magnetic beads;
5) the sample was placed on a magnetic stand for 5 min to separate the mRNA and total RNA, and the supernatant was removed;
6) the sample was taken out of the magnetic stand, added with 200 μL of Beads wash buffer, mixed well with a pipette, and then placed on the magnetic stand for 5 min, and the supernatant was removed;
7) the sample was taken out of the magnetic stand, added with 50 μL of Tris Buffer to resuspend the magnetic beads, and mixed evenly by pipetting;
8) the sample was added in a PCR machine at 80° C. for 2 min, and maintained at 25° C. to elute the mRNA;
9) 50 μL of Bead Binding Buffer was added to the sample and pipetted with a pipette to mix well;
10) the sample was placed at room temperature for 5 min to allow the mRNA to bind the magnetic beads;
11) the sample was placed on the magnetic stand for 5 min to separate the mRNA and total RNA, and the supernatant was removed; and
12) the sample was taken out of the magnetic stand, added with 200 μL of Beads Wash buffer, mixed well, then placed on the magnetic stand for 5 min, and the supernatant was removed to obtain the total mRNA.

Transcriptome Library Construction:

Library construction was conducted using the MGI transcriptome library kit. PE150 sequencing was conducted using the MGIseq-2000 high-throughput sequencing platform. The sequencing data was aligned to a human transcriptome reference sequence using a FANSe3 alignment algorithm, with a parameter of -L80-E5-10-S14-B1-U0.

Screening and Enrichment Analysis of Differential Genes:

The differentially expressed genes (up- and down-regulation more than 2 times, P less than 0.05) of the two sets of transcriptome sequencing data were selected using edgeR. The KEGG database was used to conduct gene function and pathway enrichment analysis on the down-regulated genes, and representative pathways with P value of less than 0.01 were displayed.

Figure 7:
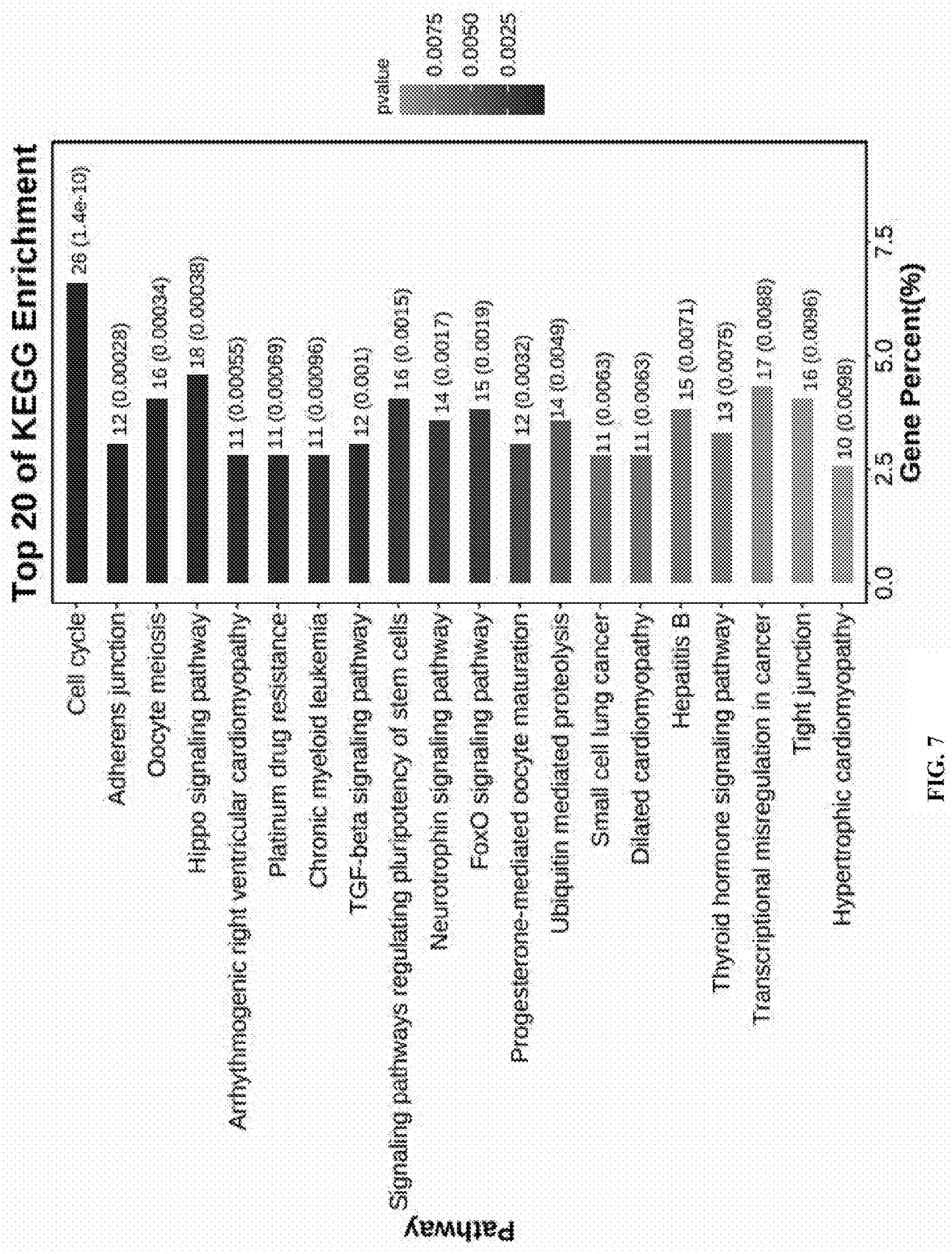
FIG. 7 shows that ATCA inhibits signaling pathways related to the malignant phenotypes of cancer, and specifically shows results of KEGG pathway enrichment of down-regulated genes after 48 h of drug treatment.

As shown in FIG. 7, the most significantly down-regulated pathway was cell cycle, which was one of the most important pathways for cancer cells to maintain rapid proliferation and growth. In addition, significantly down-regulated pathways included platinum drug-resistance, TGF-beta signaling pathway, signaling pathways regulating pluripotency of stem cells, and FoxO signaling pathway, which were pathways that contributed significantly to the oncogenesis and cancer development. This indicated that ATCA could comprehensively inhibit these cancer-promoting pathways and effectively suppress the malignant phenotype of cancer cells.

In addition, an LDH assay was adopted to determine the cytotoxicity of ATCA and detect the cytotoxicity of the drug. The results showed that at a concentration of 0.5 mg/mL, ATCA did not cause obvious cytotoxicity to cancer cells and normal cells, and the normal cells showed normal physiological activities of HBE. This proved that the ATCA had no obvious cytotoxicity.

In the experiment of ATCA inducing apoptosis in lung cancer cells, Annexin V and propidium iodide were used to stain the cancer cells and then detected by flow cytometry. Under the treatment of 0.5 mg/mL ATCA, lung adenocarcinoma cells A549 and H1299 showed significant apoptosis ($P<0.05$, $n=4$), while normal lung cells HBE did not show apoptosis. This indicated that ATCA could trigger cancer cell apoptosis without killing normal cells.

In addition, in other experiments, the ATCA could also induce apoptosis of ovarian cancer cells and inhibit the proliferation of liver cancer cells.

The above are preferred examples of this application, but the protection scope of this application is not limited thereto. Therefore, all equivalent changes made in accordance with the structure, shape, and principle of this application shall fall within the protection scope of this application.

What is claimed is:

1. A method for inhibiting a tumor using a drug target, wherein the drug target is a eukaryotic initiation factor 2 (EIF2).

2. The method according to claim 1, wherein the drug target is an EIF2 subunit 1 (EIF2S1).

3. The method according to claim 1, wherein a drug is an EIF2 inhibitor selected from the group consisting of aurintricarboxylic acid (ATCA) and an ammonium salt thereof.

4. The method according to claim 1, wherein the tumor is a malignant tumor selected from the group consisting of a malignant epithelial tumor, sarcoma, myeloma, leukemia, lymphoma, melanoma, a head and neck tumor, a brain tumor, peritoneal cancer, a mixed tumor, and a malignant childhood tumor.

5. The method according to claim 4, wherein the malignant epithelial tumor is selected from the group consisting of lung cancer, breast cancer, liver cancer, pancreatic cancer, colorectal cancer, gastric cancer, gastroesophageal adenocarcinoma, esophageal cancer, small intestine cancer, esophageal and cardiac cancer, endometrial cancer, ovarian cancer, fallopian tube cancer, vulvar cancer, testicular cancer, prostate cancer, penile cancer, kidney cancer, bladder cancer, anal cancer, gallbladder cancer, bile duct cancer, teratoma, and cardiac tumor.

6. The method according to claim 4, wherein the tumor is lung cancer, preferably non-small cell lung cancer.

7. The method according to claim 4, wherein the tumor is ovarian cancer, preferably ovarian epithelial cancer.

8. The method according to claim 4, wherein the tumor is liver cancer.

* * * * *